US008232305B2

(12) United States Patent
Elder et al.

(10) Patent No.: US 8,232,305 B2
(45) Date of Patent: Jul. 31, 2012

(54) ANTI-MICROBIAL COMPOSITIONS

(75) Inventors: Stewart Todd Elder, Butler, NJ (US); Andrea Preuss, Basel (CH); Kai-Uwe Schöning, Oberwil (CH); Karin Mühlbauer, Lörrach (DE)

(73) Assignee: BASF SE, Ludwigshafen (DE)

( * ) Notice: Subject to any disclaimer, the term of this patent is extended or adjusted under 35 U.S.C. 154(b) by 1278 days.

(21) Appl. No.: 11/811,316

(22) Filed: Jun. 8, 2007

(65) Prior Publication Data
US 2008/0070966 A1 Mar. 20, 2008

Related U.S. Application Data

(60) Provisional application No. 60/813,645, filed on Jun. 14, 2006.

(51) Int. Cl.
*A61K 31/4162* (2006.01)
*A61K 8/02* (2006.01)
(52) U.S. Cl. .................. 514/396; 514/585; 424/401
(58) Field of Classification Search .................. None
See application file for complete search history.

(56) References Cited

U.S. PATENT DOCUMENTS

| | | | | |
|---|---|---|---|---|
| 5,280,042 A * | 1/1994 | Lopes | | 514/557 |
| 5,585,343 A * | 12/1996 | McGee et al. | | 512/1 |
| 5,958,408 A | 9/1999 | Griffiths et al. | | 424/133.1 |
| 6,071,866 A | 6/2000 | Fujiwara et al. | | 510/130 |
| 6,090,772 A | 7/2000 | Kaiser et al. | | 510/388 |
| 6,358,906 B1 | 3/2002 | Ochs et al. | | 510/382 |
| 7,015,228 B2 | 3/2006 | Haap et al. | | 514/256 |
| 2005/0169852 A1 | 8/2005 | Roberge et al. | | 424/49 |
| 2006/0166856 A1 | 7/2006 | Petrat et al. | | 512/2 |

FOREIGN PATENT DOCUMENTS

| | | |
|---|---|---|
| AT | 322546 | 5/1975 |
| WO | 96/06152 | 2/1996 |
| WO | WO 2004035018 A2 * | 4/2004 |

OTHER PUBLICATIONS

Gathergood et al., "Biodegradable ionic liquids: Par I. Concept, preliminary targets and evaluation," Green Chem., 2004, 6, pp. 166-175.*
Abstract No. 2003:632645 for J. Pernak et al., Ionic Liquids with Alkoxymethyl Substituent—Synthesis and Properties, Abstracts of Papers, 226th ACS National Meeting, New York, NY, Sep. 7-11, 2003.
J. Pernak et al., The Royal Society of Chemistry, Green Chem., (Jun. 2004), 6, pp. 323-329.
J. Pernak et al., Journal of Surfactants and Detergents, vol. 6, No. 2, (Apr. 2003), pp. 119-123.
Chem. Abstract 83:114410 for AT 322546, (May 1975).

* cited by examiner

*Primary Examiner* — Yong Chong
*Assistant Examiner* — Jody Karol
(74) *Attorney, Agent, or Firm* — Shiela A. Loggins; Joseph Suhadolnik

(57) ABSTRACT

Anti-microbial compositions comprising certain imidazolium ionic liquids and non-ionic or anionic surfactants and methods of using said compositions in the preservation of personal care and cosmetic applications are provided.

18 Claims, No Drawings

ANTI-MICROBIAL COMPOSITIONS

This application claims benefit under 35 USC 119(e) of U.S. provisional application No. 60/813,645, filed Jun. 14, 2006, incorporated herein in its entirety by reference.

This invention provides anti-microbial compositions comprising certain imidazolium ionic liquids and non-ionic or anionic surfactants and methods of using said compositions in the preservation of personal care and cosmetic applications.

Anti-microbial compounds are widely used and accepted as part of numerous commercial products and materials. Antibacterial soaps, anti-fungal treatments for plants, topical medical treatments, anti-fouling coatings and disinfecting cleaners are just a few common uses of anti-microbial materials.

Anti-microbials are also common as preservatives in a wide variety of industrial, commercial and household and personal care preparations.

For example, U.S. Pat. Nos. 5,958,408; 6,090,772; 6,071,866; 6,358,906, incorporated herein in their entirety by reference, and WO96/06152 disclose compositions useful in personal applications comprising triclosan as an anti-bacterial agent.

U.S. Pat. No. 7,015,228 discloses 4-amino-2-(2-pyridyl) pyrimidines, incorporated herein in its entirety by reference, as substances suitable for the antimicrobial treatment of surfaces and the preservation of personal care preparations.

Quaternary ammonium salts are quite commonly used in anti-microbial applications and as preservatives. While frequently encountered in household and personal care preparations, quaternary ammonium salts are known to loose a significant portion of their anti-microbial activity when used in the presence of non-ionic and anionic surfactants, see for example US Pub. Pat. Appl. No. 2005/1069852, incorporated herein in its entirety by reference. This is a significant drawback given the ubiquitous use of these surfactants in household and personal care preparations.

Ionic liquids in general are understood to be a liquid consisting exclusively of ions. Ionic liquids tend to be liquid at lower temperatures than salt melts and are generally of low viscosity at low temperatures, e.g. <100° C. Ionic liquids are very useful as solvents, catalysts and surfactants. US Pub. Pat. Appl. No. 2006/166856, incorporated herein in its entirety by reference, for example, discloses the use of ionic liquids as fixatives in fragrance compositions.

Ionic liquids, such as those containing imidazolium cations, are also effective as anti-microbial agents. Pernak et.al., report on air and water stable ionic liquids consisting of 1,3-disubstituted imidazolium cations which are active against bacteria and fungi. The activity of different imidazolium cations is affected by chain lengths of the alkoxymethyl substituents used. Shorter substituents result in a lack of activity against cocci, rods and fungi; 1-methyl-3-octyloxymethylimidazolium tetrafluoroborate being the most effective of the ionic liquids tested. *Ionic liquids with alkoxymethyl substitutent—synthesis and properties* Pernak, Juliusz; Stopa, Janina; Pernak, Agnieszka M. Abstracts of Papers, 226th ACS National Meeting, New York, N.Y., United States, Sep. 7-11, 2003 (2003), American Chemical Society, Washington, D.C.

Aforementioned US Pub. Pat. Appl. No. 2006/166856 also notes that some ionic liquids may also impart antimicrobial activity to the fragrance compositions therein. However, while the fragrance compositions of US Pub. Pat. Appl. No. 2006/166856 are generically disclosed in a variety of home and personal care applications, there are no examples containing anionic surfactants, no data regarding the potential anti-microbial activity of the exemplified formulations and no mention of the potential impact of non-ionic or anionic surfactants on the antimicrobial activity.

It has been found that, unlike quaternary ammonium salts, certain ionic liquids containing imidazolium cations retain high anti-microbial activity against gram-positive bacteria, gram-negative bacteria and in particular fungi, in the presence of non-ionic and anionic surfactants. Also, unlike quaternary ammonium salts, ionic liquids are readily formulated with anionic surfactants and do not suffer the same complexation encountered between anionic materials and quaternary ammonium salts.

Anti-microbial compositions comprising these ionic liquids and non-ionic or anionic surfactants are useful as preservatives in a variety of applications, for example home and personal care applications, and are the basis of the present invention. Given the stringent demands balancing anti-microbial activity with human and animal toxicity, the use of these compositions in personal care applications is of particular interest.

DESCRIPTION OF THE INVENTION

The present invention provides anti-microbial compositions comprising non-ionic or anionic surfactants and an ionic liquid comprising a compound of formula (I):

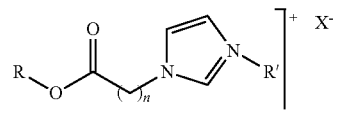

wherein

R is $C_{1-18}$ alkyl or $C_{3-18}$ alkenyl, for example $C_{8-18}$ alkyl, for example $C_{12}$ alkyl;

R' is $C_{1-18}$ alkyl or $C_{2-18}$ alkenyl, for example $C_{1-4}$ alkyl, for example methyl;

n is 1, 2, 3, 4, 5, or 6, for example n is 1;

$X^-$ is an anion;

which anti-microbial compositions are effective against gram positive bacteria, gram negative bacteria, yeasts, molds or fungi.

The present invention also provides a method for preserving personal care preparations containing non-ionic or anionic surfactants by incorporating an ionic liquid comprising a compound of formula (I).

The present invention also provides a method for preserving personal care preparations by incorporating a composition comprising a non-ionic or anionic surfactant and an ionic liquid comprising a compound of formula (1).

The present invention provides personal care preparations comprising a non-ionic or anionic surfactant and an ionic liquid comprising a compound of formula (1).

More than one compound of formula (I) may be present and other antimicrobial agents of use in personal care applications may also be present. More than one anionic or non-ionic surfactant may be present and mixtures of anionic and non-ionic surfactants may also be used.

In particular embodiments of the invention, at least one anionic surfactant is present.

Other materials including cationic surfactants may be present depending on the application.

Examples of $C_{1-18}$ alkyl include linear or branched alkyl radicals, for example methyl, ethyl, n-propyl, isopropyl, n-butyl, sec-butyl, tert-butyl, amyl, isoamyl or tert-amyl, hexyl, heptyl, octyl, isooctyl, nonyl, decyl, undecyl, dodecyl, tetradecyl, pentadecyl, hexadecyl, heptadecyl or octadecyl and the like.

Examples of $C_{2-18}$ alkenyl or $C_{3-18}$ alkenyl include linear or branched alkenyl radicals which contain one or more carbon-carbon double bonds, for example ethenyl, n-propenyl, n-butenyl, sec-butenyl, n-hexenyl, n-octenyl, n-hexadienyl, n-octadienyl, 2-ethylhexenyl, n-nonenyl, n-decenyl, n-undecenyl, n-dodecenyl, n-tridecenyl, n-tetradecenyl, n-hexadecenyl, n-octadecenyl, n-dodecadienyl, n-tetradecadienyl, n-hexadecadienyl, n-hexadecatrienyl, n-octadecadienyl or n-octadecatrienyl and the like.

Typically, R or R' is a linear alkyl. For example, R is a linear alkyl of from 8 to 18 carbon atoms and R' is methyl, ethyl, propyl, or butyl.

It is known that the length of the alkyl chains in formula (I), i.e., R and R', impact the anti-microbial activity of ionic liquids, in particular the anti-fungal activity. Compounds of formula (I) where R' is methyl, n is 1 and R is $C_{8-18}$ alkyl, for example R is dodecyl, are quite effective in the present invention, for example:

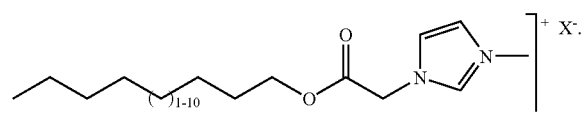

The anion $X^-$ can be any convenient anion, for example, halide, sulfate, hydrogensulfate, alkylsulfate, arylsulfate, perfluoro alkyl- and arylsulfates, sulfonate, alkylsulfonate, arylsulfonate, perfluoro alkyl- and arylsulfonates, phosphate, halophosphate, alkylphosphate, nitrate, perchlorate, tetrachloroaluminate, tetrafluoroborate, alkylborate, saccharinate, alkyl carboxylates or bis(perflouroalkylsulfonyl)anions.

For example, the anion is a halogen free anion, such as sulfate, hydrogensulfate, alkylsulfate, arylsulfate, sulfonate, alkylsulfonate, arylsulfonate, phosphate, alkylphosphate, nitrate, alkylborate, saccharinate or alkyl carboxylates.

For example, the anion is an alkyl or aryl sulfate such as tosylate, mesylate or octyl sulfate.

The imadazolium salts of the instant invention are prepared by known methods. For example a halocarboxyester, such as an alkyl 2-haloacetate, for example octyl bromoacetate, is reacted with a 1-alkyl imidazole, such as methyl imidazole, to generate the 1,3-disubstituted imidazolium halide salt. Alternately, a halo acid can be used in place of the halocarboxyester followed by esterification. If desired, transesterification reactions or changing the counter ion can be accomplished via known means.

More details relating to the preparation process according to the invention can be found in the corresponding Examples.

The imadazolium ionic liquids used in accordance with the invention exhibit pronounced antimicrobial action, for example against pathogenic gram-positive bacteria, gram-negative bacteria, yeasts and moulds. They are effective against fungi and, most importantly, they retain their effectiveness against fungi even when in the presence of non-ionic or anionic surfactants. Typical antimicrobial quaternary ammonium compounds are known to be incompatible with anionic surfactants and will lose activity.

They are accordingly suitable as antimicrobial active substances and preservatives in personal care preparations, including cosmetic products and household products, for example shampoos, bath additives, skin and hair care preparations, liquid and solid soaps, lotions, creams, deodorants and other aqueous or alcoholic solutions. Their activity in the presence of anionic surfactants is striking.

Non-ionic and anionic surfactants are widely known in the art.

A wide variety of anionic surfactants are potentially useful herein. Several examples of suitable anionic surfactants are disclosed in U.S. Pat. No. 3,929,678, which is incorporated herein by reference.

Examples of anionic surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention. Alkyl and alkyl ether sulfates have the respective formulae $R_1$—O—$SO_3$-M and $R_1$—$(CH_2H_4$—O$)_x$—$SO_3$-M, wherein $R_1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Common examples of alkyl sulfates include sodium, ammonium, potassium, magnesium, or TEA salts of lauryl or myristyl sulfate. Common examples alkyl ether sulfates include ammonium, sodium, magnesium, or TEA laureth-3 sulfate.

Another suitable class of anionic surfactants are the sulfated monoglycerides of the formula $R_1$—CO—O—$CH_2$—C(OH)H—$CH_2$—O—$SO_3$-M, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R_1SO_3$-M, wherein $R_1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of a-olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}/C_{16}$ α-olefin sulfonate.

Other suitable anionic surfactants are the linear alkylbenzene sulfonates of the form $R_1$—$C_6H_4$—$SO_3$-M, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants include the primary or secondary alkane sulfonates of the form $R_1$—$SO_3$-M, wherein $R_1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}$-$C_{17}$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, also known as 2-aminoethane-sulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable are the acyl isethionates. The acyl isethionates typically have the formula $R_1$—CO—O—$CH_2$—$CH_2SO_3$-M, wherein $R_1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Non-limiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R_1$—$OCH_2$—C(OH)H—$CH_2$—$SO_3$-M, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R_1$—CH($SO_4$)—COOH and sulfonated methyl esters of the from $R_1$—CH($SO_4$)—CO—O—$CH_3$, where $R_1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulphur trioxide or by another known sulfonation technique. Examples include alpha sulphonated coconut fatty acid and lauryl methyl ester.

Other anionic materials useful as surfactants include alkyl ether carboxylates corresponding to the formula $R_1$—($OCH_2CH_2$)$_x$—$OCH_2$—$CO_2$-M wherein $R_1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials useful as surfactants include acyl lactylates corresponding to the formula $R_1$—CO—[O—CH($CH_3$)—CO]$_x$—$CO_2$-M wherein $R_1$ is a saturated or unsaturated, branched or unbranched alkyl or alkenyl group of about 8 to about 24 carbon atoms, x is 3, and M is a water-soluble cation, non-limiting examples of which include sodium cocoyl lactylate.

Other anionic materials useful as surfactants include the carboxylates, nonlimiting examples of which include sodium lauroyl carboxylate, sodium cocoyl carboxylate, and ammonium lauroyl carboxylate. Anionic flourosurfactants can also be used.

Other anionic materials include acyl glutamates corresponding to the formula $R_1$—CO—N(COOH)—$CH_2CH_2$—$CO_2$-M wherein $R_1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R_1$—CON($CH_3$)—$CH_2CH_2$—$CO_2$-M wherein $R_1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Any counter cation, M, can be used on the anionic surfactant. Typically the counter cation is selected from the group consisting of sodium, potassium, ammonium, monoethanolamine, diethanolamine, and triethanolamine.

Typical non-ionic surfactants are condensated products of ethylene oxide with various reactive hydrogen-containing compounds reactive therewith having long hydrophobic chains (e.g. aliphatic chains of about 12-20 carbon atoms), which condensation products ("ethoxamers") contain hydrophilic polyoxyethylene moieties, such as condensation products of poly(ethyleneoxide) with fatty acids, fatty alcohols, fatty amides, polyhydric alcohols (e.g. sorbitan monostearate) and polypropylene oxide. Polyoxamers are e.g. block copolymers of polyoxyethylene and polyoxypropylene having an average molecular weight from about 3000 to 5000 and a preferred average molecular weight from about 3500 to 4000 and containing about 10-80% hydrophilic polyoxyethylene groups, by weight, of the block copolymer.

As amphoteric surfactants $C_8$-$C_{18}$-betains, $C_8$-$C_{18}$-sulfobetains, $C_8$-$C_{24}$-alkylamido-$C_1$-$C_4$-alkylene betaines, imidazoline carboxylates, alkylamphocarboxycarbonic acids, alkylamphocarbonic acid (e.g. lauroamphoglycinate) and N-alkyl-β-aminopropionate or -iminodipropionate can be used. In particular the $C_{10}$-$C_{20}$-alkylamido$C_1$-$C_4$-alkylenbetaine and coco fatty acid amide propylbetaine.

Examples of non-ionic surfactants include the zwitterionic and amphoteric surfactants of U.S. Pat. Nos. 2,658,072, 2,438,091, and 2,528,378, which are incorporated herein by reference.

The invention accordingly relates also to a personal care preparation comprising at least one compound of formula (1), an anionic or non-ionic surfactant, and cosmetically tolerable carriers or adjuvants.

Depending upon the form of the personal care preparation, the amount of ionic liquid and anionic or nonionic surfactant of the present invention will vary and may comprise a majority of the preparation. Typically, the personal care preparation according to the invention contains from about 0.01 to about 30% by weight, for example from about 0.1 to about 20% by weight, for example from about 0.1 to about 15% by weight based on the total weight of the composition, of a mixture of the ionic liquid and anionic or nonionic surfactant of the present invention and cosmetically tolerable adjuvants.

The antimicrobial agents of the present invention can be used as ingredients in a wide variety of cosmetic preparations. There come into consideration, for example, especially the following preparations like skin-care preparations, bath preparations, cosmetic personal care preparations, foot-care preparations; light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations or cosmetic hair-treatment preparations.

Cosmetic formulations, for clarity, cosmetic formulations, personal care preparations and cosmetic preparations are used interchangeably throughout, according to the invention are used in various fields, for example: skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts; skin-care preparations, e.g. skin emulsions, multi-emulsions or skin oils; cosmetic personal care preparations, e.g. facial make-up in the form of day creams or powder creams, face powder (loose or pressed), rouge or cream make-up, eye-care preparations, e.g. eye shadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers; intimate hygiene preparations, e.g. intimate washing lotions or intimate sprays; foot-care preparations, e.g. foot baths, foot powders, foot creams or foot balsams, special deodorants and antiperspirants or callus-removing preparations; light-protective preparations, such as sun milks, lotions, creams or oils, sun-blocks or topicals, pre-tanning preparations or after-sun preparations; skin-tanning preparations, e.g. self-tanning creams; depigmenting preparations, e.g. preparations for bleaching the skin or skin-lightening preparations; insect-repellents, e.g. insect-repellent oils, lotions, sprays or sticks; deodorants, such as deodorant sprays, pump-action sprays, deodorant gels, sticks or roll-ons; antiperspirants, e.g. antiperspirant sticks, creams or roll-ons; preparations for cleansing and caring for blemished skin, e.g. synthetic detergents (solid or liquid), peeling or scrub preparations or peeling masks; hair-removal preparations in chemical form (depilation), e.g. hair-removing powders, liquid hair-removing preparations, cream or paste-form hair-removing preparations, hair-removing preparations in gel form or aerosol foams; shaving preparations, e.g. shaving soap, foaming shaving creams, non-foaming shaving creams, foams and gels, preshave preparations for dry shaving, aftershaves or aftershave lotions; fragrance preparations, e.g. fragrances (eau de Cologne, eau de toilette, eau de parfum, parfum de toilette, perfume), perfume oils or perfume creams; dental care, denture-care and mouth-care preparations, e.g. toothpastes, gel toothpastes, tooth powders, mouthwash concentrates, anti-plaque mouthwashes, denture cleaners or denture fixatives; cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

Depending upon the form of the personal care preparation, it comprises, in addition to the ionic liquid comprising a compound of formula (1) and an anionic or non-ionic surfactant further constituents, for example sequestering agents, colorings, perfume oils, thickening or solidifying agents (consistency regulators), emollients, UV-absorbers, skin protective agents, antioxidants, chelating agents, additives that improve the mechanical properties, such as dicarboxylic acids and/or aluminum, zinc, calcium or magnesium salts of fatty acids, stabilizers and additional preservatives.

Examples of such formulations and the materials incorporated therein are widely known in the art can be found, for example, in United States Patent Appl. Pub. No. 20030186834, which application is hereby incorporated in its entirety by reference.

A shampoo has, for example, the following composition: 0.01 to 5% by weight of a compound of formula (1), 12.0% by weight sodium laureth-2-sulfate, 4.0% by weight cocamidopropyl betaine, 3.0% by weight NaCl and water ad 100%.

A deodorant has, for example, the following composition: 0.01 to 5% by weight of a compound of formula (1), 60% by weight ethanol, 0.3% by weight perfume oil, and water ad 100%.

Antimicrobials which can additionally be used along with the compositions and methods of the present invention are widely known in the field and include: Pyrithiones, Dimethyldimethylol Hydantoin, Methylchloroisothiazolinone/methylisothiazolinone, Sodium Sulfite, Sodium Bisulfite, Imidazolidinyl Urea, Diazolidinyl Urea, Benzyl Alcohol, 2-Bromo-2-nitropropane-1,3-diol, formaldehyde, Iodopropenyl Butylcarbamate, Chloroacetamide, Methanamine, Methyldibromonitrile Glutaronitrile (1,2-Dibromo-2,4-dicyanobutane), Glutaraldehyde, 5-bromo-5-nitro-1,3-dioxane, Phenethyl Alcohol, o-Phenylphenol/s, for example, commonly encountered compounds such as farnesol, parfumes, phenoxyethanol, quaternary compounds, triclosan, triclocarban, organic acids such as benzoic acid or sorbic acid, biguanides such as poly-(hexamethylene biguanide)hydrochloride phenoxypropanol, benzalkonium chloride, cetrimonium bromide or benzethonium chloride or salicylic acid and the like.

Another class of antibacterial agents, which can additionally be used, are the so-called "natural" antibacterial actives, referred to as natural essential oils.

Additional active agents are antibacterial metal salts. This class generally includes salts of metals in groups 3b-7b, 8 and 3a-5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

The antimicrobial compositions of the present invention may also comprise a proton donating agent, such as acids, for example mineral acids and organic acids, salts thereof, and mixtures thereof.

In order to achieve the mildness required of the antimicrobial composition of the present invention, optional ingredients to enhance the mildness to the skin can be added. These ingredients are well known in the filed and include synthetic and naturally occurring polymers, co-surfactants and moisturizers.

For example, lipophilic skin conditioning agents may be present, for example, hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. Nos. 3,600,186; 4,005,195 and 4,005,196, all of which are herein incorporated by reference, or blends of liquid digestible or nondigestible oils with solid polyol polyesters such as those described in U.S. Pat. Nos. 4,797,300; 5,306,514; 5,306,516 and 5,306,515, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof.

Nonlimiting examples of silicone useful herein are described in U.S. Pat. No. 5,011,681, to Ciotti et al., issued Apr. 30, 1991, which is incorporated by reference.

Nonlimiting examples of naturally occuring oils include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters may be used and an example is acetylated monoglycerides.

When a lipophilic skin moisturizing agent is employed as the mildness enhancer in the antimicrobial compositions herein, a stabilizer may also be included. The stabilizer is used to form a crystalline stabilizing network in the liquid composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability. Typical hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin).

Alternatively, the stabilizer employed in the antimicrobial compositions herein can comprise for example a polymeric thickener, a $C_{10}$-$C_{22}$ ethylene glycol fatty acid ester, dispersed amorphous silica, dispersed smectite clay such as bentonite and hectorite, a fatty acid or fatty alcohol.

The antimicrobial compositions of the present invention can comprise a wide range of optional ingredients. The CTFA International Cosmetic Ingredient Dictionary, Sixth Edition, 1995, which is incorporated by reference herein in its entirety, describes a wide variety of materials commonly used in the cosmetic and personal care industry suitable for use in the compositions of the present invention. Nonlimiting examples of functional classes of ingredients are described at page 537 of this reference.

Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

The personal care preparation according to the invention may exist in a wide variety of presentation forms, for example a water-in-oil or oil-in-water emulsion, an alcoholic or alcohol-containing formulation, a vesicular dispersion of an ionic or non-ionic amphiphilic lipid, a gel, a solid stick, cream, milk or lotion, a powder, a lacquer, a tablet or make-up, a stick, a spray or an aerosol, a foam, or a paste and all kinds of microemulsions.

As a water-in-oil (W/O) or oil-in-water emulsion (O/W), the cosmetically tolerable adjuvant typically contains from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a small chain or fatty alcohol including mono- and poly-ols, e.g., ethanol, isopropanol, propylene glycol, hexylene glycol, glycerol and sorbitol.

The aqueous phase contains for example ingredients such as alcohols, diols or polyols or their ethers as well as one or more thickeners for example of the groups of silicium dioxide, aluminium silicates, polysaccharides or derivatives thereof for example hyaluronic acid, xanthan gum, hydroxypropylmethylcellulose, polyacrylates.

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones.

The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which patent is incorporated herein by reference. The compositions of the invention may also include silicone polymer materials, which provide both style retention and conditioning benefits to the hair. Such materials are described in U.S. Pat. No. 4,902,499, which is incorporated herein by reference.

EXAMPLES

Example 1

Preparation of Octyl 2-bromoacetate

Finely ground potassium carbonate (41.1 g) is added to a stirred dioxane solution of Octyl alcohol (36.9 g) cooled by an ice bath followed by addition over approximately 15 minutes of 2-bromoacetyl bromide (40.0 g). The mixture is stirred overnight, filtered and the dioxane is removed under vacuum. The residue is taken up in dichloromethane, washed with 10% HCl, water, sodium bicarbonate, and dried over magnesium sulfate. After removal of the solvent, the product is obtained as a light yellow oil.

Example 2

Preparation of 1-methyl-3-(2-oxo-2-octyloxyethyl)-1H-Imidazolium bromide

Methyl imidazol (18.1 g) in 20 ml diethyl ether is added drop wise to a stirred mixture of Octyl-2-bromoacetate (55.7 g) and diethyl ether (200 ml) and cooled to 0° C. in an ice bath. The mixture is stirred overnight to yield a two phase mixture. The top ether layer is decanted and the product is stirred in 100 ml of fresh diethyl ether for 10 minutes. The ether layer is again decanted. The product is washed in this manner 5 times to yield, after drying under vacuum, the product as a white waxy solid.

The following examples are prepared according to the procedures of Examples 1 and 2 from the corresponding alcohol.

| Example | Ester | Alcohol used | % Yield |
|---|---|---|---|
| 3 | Butyl | 1-Butanol | 87% |
| 4 | Dodecyl | 1-Dodecanol | 81% |
| 5 | Hexadienyl | 1-Hexadienol | 87% |
| 6 | Octadecyl | 1-Octadecanol | 65% |

Example 7

Microbicidal Activity According to EN1040

A bacterial suspension with a cell count of about $10^7$ cfu/ml is contacted with appropriate concentrations of the specific substances and the residual cell count determined after incubation times of 5 and 30 minutes at room temperature under continuous stirring. *Staphylococcus aureus* was tested as gram+ and *Escherichia coli* as gram− organism. The results are given as a log reduction in comparison to a growth control in water.

| Sample | *S. aureus* | | *E. coli* | |
|---|---|---|---|---|
| (1000 ppm) | 5 min. | 30 min. | 5 min. | 30 min. |
| Butyl ester Ex 3 | <1 | <1 | <1 | <1 |
| Octyl ester Ex 2 | 3.2 | 3.7 | <1 | 1.2 |
| Dodecyl ester Ex 4 | >5 | >5 | >5 | >5 |

Example 8

Microbicidal Activity Under Conditions Similar to a Preservative Challenge Test The test procedure of Example 7 is used, with an inoculum concentration of $10^5$ cfu/ml and incubation times of 48 and 72 hours; figures given as log reduction.

| | | *P. aeruginosa* ATCC 15442 | | *E. coli* ATCC 10536 | | *S. aureus* ATCC 6538 | | *C. albicans* ATCC 10231 | | *A. niger* ATCC 16404 | |
|---|---|---|---|---|---|---|---|---|---|---|---|
| Sample | Conc. | 48 h | 72 h | 48 h | 72 h | 48 h | 72 h | 48 h | 72 h | 48 h | 72h |
| Ex 3 | 0.5% | >3 | >3 | >3 | >3 | >3 | >3 | 1.4 | 1.7 | <1 | <1 |
| Ex 2 | 0.5% | >3 | >3 | >3 | >3 | >3 | >3 | >3 | >3 | 1.8 | 2.3 |
| Ex 4 | 0.5% | >3 | >3 | >3 | >3 | >3 | >3 | >3 | >3 | 1.8 | 2.3 |

Example 9

Antifungal Activity

Fungicidal activity is tested according to EN12175. A fungal spore suspension with a spore cell count of about $10^6$ cfu/ml is contacted with appropriate concentrations of the specific substances and the residual spore cell count determined after incubation times of 30 and 60 minutes at room temperature under continuous stirring. *Penicillium funiculosum*, *Aspergillus niger* and *Aureobasidium pullulans* are tested as important mold strains.

The results are given as a log reduction at each incubation time in comparison to a water control.

| | | *P. funiculosum* | | *A. niger* | | *A. pullulans* | |
|---|---|---|---|---|---|---|---|
| Sample | | 30 min | 1 h | 30 min | 1 h | 30 min | 1 h |
| Butyl Ex 3 | 30' | <1 | | <1 | | <1 | |
| 1% | 1 h | | <1 | | <1 | | <1 |
| Octyl Ex 2 | 30' | <1 | | <1 | | >4 | |
| 1% | 1 h | | <1 | | 2.0 | | >4 |
| Dodecyl Ex 4 | 30' | <1 | | 2.1 | | >4 | |
| 1% | 1 h | | 1.9 | | >4 | | >4 |

Example 10

Preservative Challenge Test

A preservative challenge test is conducted for representative cosmetic formulations according to the conditions of the EurPh and USP. The compound concentration in the formulations is 0.5% w/w. The Inoculum concentration of the five different strains is $2.1\text{-}4.2\times10^5$ cfu/ml, incubation time according to EurPh. 2, 7, 14 and 28 days. Preservation is investigated in two different emulsion types, w/o and o/w.

W/O Emulsion:

| Part A | Paraffin Liquidum | 7.50 |
|---|---|---|
| | Isohexadecane | 6.00 |
| | PEG-7 Hydrogenated Castor Oil | 4.10 |
| | Isopropyl Palmitate | 2.00 |
| | Cera Microcristallina | 0.50 |
| | Lanolin Alcohol | 0.60 |
| Part B | Aqua | Qs to 100 |
| | Magnesium Sulfate | 1.00 |
| | Glycerin | 3.20 |
| Part C | Methyl imidazolium bromide ester | 0.50 |

Aqua Qs to 100 means water added to bring total parts in formulation to 100

Blank Log Reduction

| Time [Days] | E. coli | P. aerug. | S. aureus | C. albicans | A. niger |
|---|---|---|---|---|---|
| 2 | 0 | 0 | 1 | 0 | 0 |
| 7 | 0 | 0 | ≧4 | 0 | 0 |
| 14 | 0 | 0 | 6 | 0 | 0 |
| 28 | 0 | 0 | 6 | 0 | 0 |

Cmpd of Ex 2—Log Reduction
0.5%

| Time [Days] | E. coli | P. aerug. | S. aureus | C. albicans | A. niger |
|---|---|---|---|---|---|
| 2 | 6 | 5 | 6 | 1 | 0 |
| 7 | 6 | 5 | 6 | ≧3 | 0 |
| 14 | 6 | 5 | 6 | 5 | 0 |
| 28 | 6 | 5 | 6 | 5 | 0 |

Cmpd of Ex 4—Log Reduction
0.5%

| Time [Days] | E. coli | P. aerug. | S. aureus | C. albicans | A. niger |
|---|---|---|---|---|---|
| 2 | 6 | 5 | 6 | 2 | 0 |
| 7 | 6 | 5 | 6 | 3 | 1 |
| 14 | 6 | 5 | 6 | 3 | 2 |
| 28 | 6 | 5 | 6 | 5 | 2 |

O/W Emulsion:

| Part A | Steareth-2 | 2.20 |
|---|---|---|
| | Steareth-21 | 1.00 |
| | PPG-15 Stearyl Ether | 6.00 |
| | Dicaprylyl Ether | 6.00 |
| Part B | Aqua | Qs to 100 |
| | Sodium Polyacrylate | 0.20 |
| Part C | Methyl imidazolium bromide ester | 0.50 |

Aqua Qs to 100 means water added to bring total parts in formulation to 100

Blank Log Reduction

| Time [Days] | E. coli | P. aerug. | S. aureus | C. albicans | A. niger |
|---|---|---|---|---|---|
| 2 | 0 | 0 | 1 | 0 | 0 |
| 7 | 0 | 0 | 2 | 0 | 0 |
| 14 | 0 | 0 | 3 | 0 | 0 |
| 28 | 0 | 0 | ≧4 | 0 | 0 |

Cmpd of Ex 2—Log Reduction
0.5%

| Time [Days] | E. coli | P. aerug. | S. aureus | C. albicans | A. niger |
|---|---|---|---|---|---|
| 2 | 3 | ≧4 | ≧4 | 0 | 0 |
| 7 | ≧4 | 5 | 6 | 2 | 0 |
| 14 | 6 | 5 | 6 | ≧3 | 0 |
| 28 | 6 | 5 | 6 | 5 | 0 |

Cmpd of Ex 4—Log Reduction
0.5%

| Time [Days] | E. coli | P. aerug. | S. aureus | C. albicans | A. niger |
|---|---|---|---|---|---|
| 2 | 1 | ≧4 | 4 | 0 | 0 |
| 7 | 1 | 5 | 6 | 0 | 0 |
| 14 | 2 | 5 | 6 | 0 | 0 |
| 28 | ≧4 | 5 | 6 | 0 | 0 |

No stable w/o or o/w emulsions could be formulated with comparable concentrations of the widely used, commercial anti-microbial agent, benzalkonium chloride.

Example 11-15

The following examples are prepared according to the procedures of Examples 1 and 2 starting from butyl imidazole instead of methyl imidazole, 2-chlorocetyl chloride instead of 2-bromoacetyl bromide and the corresponding alcohol.

Example 11: 1-butyl-3-(2-oxo-2-octyloxyethyl)-1H-Imidazolium chloride

Example 12: 1-butyl-3-(2-oxo-2-butyloxyethyl)-1H-Imidazolium chloride

Example 13: 1-butyl-3-(2-oxo-2-dodecyloxyethyl)-1H-Imidazolium chloride

Example 14: 1-butyl-3-(2-oxo-2-hexadienyloxyethyl)-1H-Imidazolium chloride

Example 15: 1-butyl-3-(2-oxo-2-octadecyloxyethyl)-1H-Imidazolium chloride

The compounds of Examples 11-15 show good activity when tested according to the protocols of Examples 7, 8, 9 and 10.

The invention claimed is:

1. An anti-microbial composition comprising a non-ionic or anionic surfactant and an anti-microbial ionic liquid of formula (I):

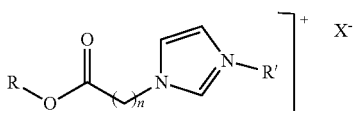

wherein
R is $C_{8-18}$ alkyl;
R' is $C_{1-4}$ alkyl;
n is 1;
$X^-$ is an anion;
which anti-microbial compositions are effective against gram positive bacteria, gram negative bacteria, yeasts, molds or fungi.

2. A composition according to claim 1, wherein R is dodecyl, R' is methyl and n is 1.

3. A method for preserving personal care preparations containing a non-ionic or anionic surfactant by incorporating an anti-microbial ionic liquid of formula (I)

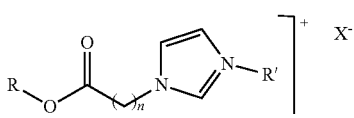

wherein
R is $C_8C_{18}$;
R' is $C_{1-4}$ alkyl;
n is 1;
$X^-$ is an anion.

4. A method according to claim 3, wherein R is $C_{8-18}$ alkyl, R' is $C_{1-4}$ alkyl and n is 1.

5. A method according to claim 3, wherein R is dodecyl, R' is methyl and n is 1.

6. A method for preserving personal care preparations by incorporating a composition comprising a non-ionic or anionic surfactant and an anti-microbial ionic liquid of formula (1):

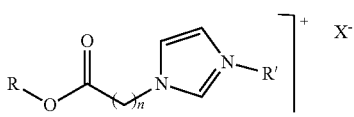

wherein
R is $C_{8-18}$ alkyl;
R' is $C_{1-4}$ alkyl;
n is 1;
$X^-$ is an anion.

7. A method according to claim 6, wherein R is dodecyl, R' is methyl and n is 1.

8. Personal care preparations comprising a non-ionic or anionic surfactant and an anti-microbial ionic liquid of formula (1)

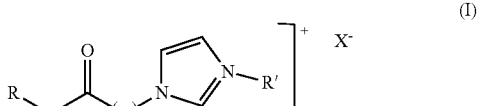

wherein
R is $C_{8-18}$ alkyl;
R' is $C_{1-4}$ alkyl;
n is 1;
$X^-$ is an anion.

9. A preparation according to claim 8, wherein R is dodecyl, R' is methyl and n is 1.

10. A preparation according to claim 8 comprising from 0.01 to 15% by weight, based on the total weight of the preparation, of the anti-microbial compound according to formula (1).

11. A composition according to claim 1, which contains an anionic surfactant.

12. A method according to claim 3, wherein the personal care preparation contains anionic surfactants.

13. A method according to claim 6, wherein the composition-contains an anionic surfactant.

14. An anti-microbial composition according to claim 1, which comprises an anionic surfactant.

15. A method for preserving a personal care preparation according to claim 3, wherein the personal care preparation comprises an anionic surfactant.

16. A method for preserving personal care preparations according to claim 6, wherein the composition comprises at least one anionic surfactant.

17. Personal care preparations according to claim 8 which comprise an anionic surfactant.

18. The composition according to claim 1, wherein
R is octyl, decyl or dodecyl;
R' is butyl and
the compound of formula (I) is effective against fungi.

* * * * *